United States Patent
Hetherington et al.

(10) Patent No.: US 11,110,069 B2
(45) Date of Patent: Sep. 7, 2021

(54) COMPOSITION COMPRISING CANNABINOIDS FOR RELIEF OF PAIN

(71) Applicant: CANOPY HEALTH INNOVATIONS, Toronto (CA)

(72) Inventors: Mark Andrew Hetherington, Toronto (CA); Chris Schnarr, Toronto (CA)

(73) Assignee: TWEED INC., Smiths Falls (CA)

( * ) Notice: Subject to any disclaimer, the term of this patent is extended or adjusted under 35 U.S.C. 154(b) by 0 days.

(21) Appl. No.: 16/671,469

(22) Filed: Nov. 1, 2019

(65) Prior Publication Data
US 2020/0138737 A1    May 7, 2020

Related U.S. Application Data

(60) Provisional application No. 62/754,984, filed on Nov. 2, 2018.

(51) Int. Cl.
| | | |
|---|---|---|
| *A61K 36/00* | (2006.01) |
| *A61K 31/05* | (2006.01) |
| *A61K 9/00* | (2006.01) |
| *A61K 31/196* | (2006.01) |
| *A61K 36/28* | (2006.01) |
| *A61K 31/192* | (2006.01) |
| *A61K 36/61* | (2006.01) |
| *A61K 31/165* | (2006.01) |
| *A61K 31/606* | (2006.01) |

(52) U.S. Cl.
CPC ............ *A61K 31/05* (2013.01); *A61K 9/0014* (2013.01); *A61K 31/165* (2013.01); *A61K 31/192* (2013.01); *A61K 31/196* (2013.01); *A61K 31/606* (2013.01); *A61K 36/28* (2013.01); *A61K 36/61* (2013.01)

(58) Field of Classification Search
None
See application file for complete search history.

(56) References Cited

U.S. PATENT DOCUMENTS

| | | | |
|---|---|---|---|
| 2009/0041857 A1* | 2/2009 | Gross | A61K 31/618 424/630 |
| 2009/0098213 A1* | 4/2009 | Tran | A61K 36/282 424/526 |
| 2016/0129066 A1* | 5/2016 | Medri | A61K 31/045 424/729 |
| 2018/0193394 A1* | 7/2018 | Sekura | A61K 31/05 |

* cited by examiner

*Primary Examiner* — Qiuwen Mi
(74) *Attorney, Agent, or Firm* — BCF LLP

(57) ABSTRACT

The present technology generally relates to compositions comprising cannabinoids for relieving pain in a subject and to methods of using such compositions for relieving pain in a subject.

17 Claims, No Drawings

COMPOSITION COMPRISING CANNABINOIDS FOR RELIEF OF PAIN

CROSS-REFERENCE TO RELATED APPLICATION

This application claims the benefit of and priority to U.S. provisional patent application No. 62/754,984, filed on Nov. 2, 2018; the content of all of which is herein incorporated in entirety by reference.

FIELD OF TECHNOLOGY

The present technology generally relates to compositions comprising cannabinoids for relieving pain in a subject and to methods of using such compositions for relieving pain in a subject.

BACKGROUND INFORMATION

Natural or synthetic cannabinoid receptor agonists have been shown to be of therapeutic value for a number of important medical conditions, including pain (e.g., against pain of neuropathic origin), anxiety, glaucoma, nausea, emesis, muscle spasms, and wasting diseases. Insofar as pain is concerned, it is known that cannabinoid receptor agonists have antinociceptive and anti-hyperalgesic effects at the peripheral and central (spinal and supraspinal) levels, as has been demonstrated in acute and chronic pain models.

Cannabinoid receptors and endocannabinoids are present in pain circuits from the peripheral sensory nerve endings up to the brain. Cannabinoid receptor agonists modulate nociceptive thresholds by regulating neuronal activity, but they also relieve pain by acting on non-nervous tissues. $CB_1$ receptor is involved in the attenuation of synaptic transmission, and a proportion of the peripheral analgesic effect of endocannabinoids can be attributed to a neuronal mechanism acting through $CB_1$ receptors expressed by primary afferent neurons. Although $CB_2$ receptors have been related traditionally to the peripheral effects of cannabinoids (mainly modulation of the immunologic responses), they also contribute to antinociception by inhibiting the release of proinflammatory factors by non-neuronal cells located near nociceptive neuron terminals. $CB_2$ receptors are expressed in several types of inflammatory cells and immunocompetent cells. For that reason, activation of peripheral $CB_2$ receptors generates an antinociceptive response in situations of inflammatory hyperalgesia and neuropathic pain.

The use of cannabinoids to alleviate pain has been proposed and tested. However, there remain many challenges associated with achieving therapeutic effectiveness of cannabinoid agonist-based medications in the management of various types of pain. There also remain many challenges with providing adequate and reproducible dosages of cannabinoids which are efficient in the management of pain.

SUMMARY OF TECHNOLOGY

According to various aspects, the present disclosure provides for compositions for topical application comprising. The compositions comprise at least one cannabinoid; and at least one anti-inflammatory agent. Optionally, the composition comprises at least one botanical extract.

According to various aspects, the present disclosure provides for methods for relieving pain in a subject, the method comprising administering to the subject the compositions as defined herein.

Other aspects and features of the present disclosure will become apparent to those ordinarily skilled in the art upon review of the following description of specific embodiments.

DETAILED DISCLOSURE OF EMBODIMENTS

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which variations and additions do not depart from the present technology. Hence, the following description is intended to illustrate some particular embodiments of the technology, and not to exhaustively specify all permutations, combinations and variations thereof.

As used herein, the singular form "a," "an" and "the" include plural referents unless the context clearly dictates otherwise.

The recitation herein of numerical ranges by endpoints is intended to include all numbers subsumed within that range (e.g., a recitation of 1 to 5 includes 1, 1.25, 1.5, 1.75, 2, 2.45, 2.75, 3, 3.80, 4, 4.32, and 5).

The term "about" is used herein, explicitly or not; every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. The term "or" as used herein should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

As used herein, the term "comprise" is used in its non-limiting sense to mean that items following the word are included, but items not specifically mentioned are not excluded.

As used herein, the term "purified" or "isolated" means isolated from a plant using chromatography, distillation, extractions, or similar technique resulting in a greater than 60% purity. In some embodiments the "purified" compounds disclosed herein have greater than 70% purity. In some embodiments the "purified" compounds disclosed herein have greater than 80% purity. In some embodiments the "purified" compounds disclosed herein have greater than 90% purity, greater than 95% purity, or greater than 98% purity. Within the context of the present disclosure, where a compound comprises stereogenic centers, the term "purified" or "isolated" includes enantiomerically pure compositions and also mixtures of enantiomers or isomers.

As used herein, the term "*Cannabis*" refers to the genus of flowering plants in the family Cannabaceae. Three species, subspecies or varieties may be recognized as being part of the *Cannabis* genus, namely: *Cannabis sativa, Cannabis indica*, and *Cannabis ruderalis*. The expressions "*Cannabis sativa*" and "*C. sativa*" are used herein interchangeably. The term "variety" as used herein refers to different chemovars or cultivars of the plant genus *Cannabis*. For example, the term "variety" can refer to different pure or hybridized *cannabis* plants. In some instances, the *cannabis* variety of the present technology can be a hybrid of two varieties, for example, a hybrid between *C. sativa* and *C. indica*. Different *cannabis* varieties often exhibit distinct chemical compositions with characteristic levels of cannabinoids and terpenes, as well as other components. Differing cannabinoid and terpene profiles associated with different *cannabis* varieties can be useful for the treatment of different diseases, or for treating different subjects with the same disease.

As used herein, the term "cannabinoid" means any substance that acts upon a cannabinoid receptor. For example, the term cannabinoid includes cannabinoid ligands such as agonists, partial agonists, inverse agonists, or antagonists, as demonstrated by binding studies and functional assays.

As used herein, the expression "effective amount" or "therapeutically effective amount" refers to the amount of components of the compositions of the present disclosure which are effective for producing some desired therapeutic effect as defined herein at a reasonable benefit/risk ratio applicable to any treatment.

As used herein an "extract" is directed to a substance, composition or compound which is obtained from a natural material, a plant-based material, or a whole plant. An extract is directed to a whole plant removed from its growth media, preferably soil. More preferably, the extract is directed to a substance, composition or compound reed from the whole plant by chemical or biological means described elsewhere herein under the recitation of separation and purification. More preferably yet, the extract is substantially free of cellulosic material or other biologically inert compositions. In this context, "substantially free of" is preferably directed to material which is independently selected to be 100%, 90%, 80%, 70%, 60%, or 50% free from plant material free of the biological effects intended. More preferably the material is directed to material which is independently selected to be 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% free of material not having the properties desired and characterized by the selection methods described herein. More preferably the material independently selected to be 100%, 99%, 98%, 97%, 96%, 95%, 94%, 93%, 92%, 91%, 90%, 89%, 88%, 87%, 86%, 85%, 84%, 83%, 82%, 81%, or 80 free of material other than those characterized by the selection methods described herein.

As used herein, the term "wt %" means weight percent, which is also written herein as "w/w". Weight percent is the weight of solute divided by the weight of solvent and multiplied by 100, to give the percent of solute in the solution. For example, 25 wt % of a compound in water means there is 25 grams of the compound for every 100 grams of water.

In some embodiments, the present technology comprises compositions for topical use in treating pain, optionally including inflammation and one or more agents capable of engaging the cannabinoid receptors. Such compositions optionally include agents capable of treating noxious stimuli effecting the nociception system. An additional embodiment of the technology further comprises compositions for the treatments above which further comprise one or more agents capable of engaging the nociceptor receptor system. Accordingly, one embodiment of the technology is directed to compositions comprising an anti-inflammatory, and one or more compounds capable of engaging the human or animal $CB_1$ or $CB_2$ receptor system. In some instances, the composition further comprises one or more compounds capable of engaging one or more nociceptor receptors.

In one embodiment, the present technology relates to compositions comprising a cannabinoid and an anti-inflammatory agent for relieving pain in a subject.

In one embodiment, the present technology relates to compositions comprising a cannabinoid, an anti-inflammatory agent and a botanical extract for relieving pain in a subject.

In one embodiment, the present technology relates to compositions comprising a cannabinoid, an anti-inflammatory agent for treating pain in a subject.

In one embodiment, the present technology relates to compositions comprising a cannabinoid, an anti-inflammatory agent and a botanical extract for treating pain in a subject.

The effect will be observable by a subject in need of pain relief, more preferably using a topical ointment, gel, cream, oil, wax, paste, fluid, patch, or transdermal delivery system, or the like.

Kits, packaging and devices for administration, use, and the like, which comprise the compositions of the present technology together with labeling or other instruction for administration, use and the like, of the compositions are also contemplated within the scope of the present technology.

In the context of the present technology the terms "engage", "engagement", "engaging," and the like, of the nociceptor system when applied to a composition, compound or extracts of the technology mean that the composition or compound affects observable properties of the nociceptor system, preferably nociceptor type A6, type I A6, type II A6, type C, group III, group IV, P2X3, and pain receptors in the peritendinous tissue, joint capsule, ligaments, proximal tendons, bone, periosteum, articular fat pad, around blood vessels, lumbar facet joint capsule and viscera. Set forth herein are two laboratory and one self-reporting survey methods for detecting engagement of the nociceptor system. In the context of the present technology the phrases "engage, engagement, engaging" and the like, the cannabinoid receptors when applied to a composition or compound mean that the composition or compound affects observable properties of the cannabinoid receptors, preferably the cannabinoid receptors engaged are those related to biological activity of cannabinoids, more preferably, the major cannabinoids, more preferably yet, the $CB_1$ and/or $CB_2$.

In the context of the present technology, the expression "dermal product" means a compound, composition, formulation, delivery system or method of providing the substance to the skin. "Dermal products" is comprehended to mean compounds or compositions which, upon delivery to the epidermis will be distributed to one or more of the following: epidermis, dermis, hypodermis, hair follicle, sweat gland, fat and connective tissue of the skin. In one embodiment, one or more compounds of the compositions will be partly or entirely distributed to the systemic circulation of the body. In some implementations, the "dermal product" is distributed in the layers of the skin with moderate to no distribution in the systemic circulation. In some implementations, one or more compounds of the compositions will be partly or entirely distributed to the lymphatic circulation of the body. In other implementations, the "dermal product" is distributed in the layers of the skin with moderate to no distribution in the lymphatic circulation.

In one embodiment, the "dermal product" comprises compounds having different distributions to exemplary compartments such as the layers of the skin, systemic and corporeal circulations. In such an embodiment, compounds are selected such that the compounds will become concentrated in the one or more compartments wherein the activity of each compound is optimum.

i) Cannabinoids

A cannabinoid is one of a class of diverse chemical compounds that acts on cannabinoid receptors such as $CB_1$ and $CB_2$ in cells that alter neurotransmitter release in the brain. Ligands for these receptor proteins include the endocannabinoids (produced naturally in the body by animals), the phytocannabinoids (found in *cannabis* and some other plants), and synthetic cannabinoids (manufactured artificially as set forth above). The most notable cannabinoid of the phytocannabinoids is tetrahydrocannabinol (THC), the primary psychoactive compound in *cannabis*. Cannabidiol (CBD) is another cannabinoid that is a major constituent of the plant. Synthetic cannabinoids and semisynthetic cannabinoids encompass a variety of distinct chemical classes: the classical cannabinoids structurally related to THC, the non-classical cannabinoids (cannabimimetics) including the aminoalkylindoles, 1,5-diarylpyrazoles, quinolines, and arylsulfonamides as well as eicosanoids related to endocannabinoids. Tetrahydrocannabinol (THC) refers to a psychotropic cannabinoid and is the principal psychoactive constituent of *cannabis*. Its chemical name is (−)-trans-$\Delta^9$-tetrahydrocannabinol and the term "THC" is used to refer to isomers as well.

In some embodiments, the cannabinoid present in the compositions of the present technology is an isolated cannabinoid.

In some embodiments, the cannabinoid present in the compositions of the present technology is a cannabinoid extract.

In some embodiments, the cannabinoid present in the compositions of the present technology is a cannabinoid distillate.

Cannabinoids contemplated to be within the scope of the present technology include: cannabigerol ((E)-CBG C-5), cannabigerol monomethyl ether ((E)-CBGM C-5A), Cannabinerolsäure A ((Z)-CBGA C-5A), Cannabigerovarin (((e)-CBGV C-3), Cannabinerolsäure A (e)-CBGA C-5A), A Cannabinerolsäure monomethyl ether ((e)-CBGAM C-5A), Cannabinerolsäure A ((e)-CBGVA-C3A); cannabichromene (CBC-C5), Cannabinerolsäure A (CBCA C-5A), Cannabichromevarin (CBCVC-3), Cannabinerolsäure A (CBCVA-C3A); cannabidiol (CBD-C5), cannabidiol monomethyl (CBDM-C5), cannabidiol-C4 (CBD-C4), Cannabidivarin (CBDV-C3), Cannabidiorcol (CBD-C1), cannabidiolic (CBDA C-5), Cannabinerolsäure (CBDVA C-3); Cannabinodiol-like (CBND): Cannabinodiol (CBND C-5), Cannabinodivarin (CBND C-3); Tetrahydrocannabinol-like (THC): $\Delta^9$-tetrahydrocannabinol ($\Delta^9$-THC-C5), $\Delta^9$-tetrahydrocannabinol-C4 ($\Delta^9$-THC-C4), $\Delta^9$-tetrahydrocannabivarin ($\Delta^9$-THCV-C3), $\Delta^9$-Tetrahydrocannabiorcol ($\Delta^9$-THCO-C-1), Δ9-Tetrahydrocannabinolsäure A ($\Delta^9$THCA-C-5A), $\Delta^9$-Tetrahydrocannabinolsäure B ($\Delta^9$THCA-C-5B), $\Delta^9$-Tetrahydrocannabinolsäure-C4 ($\Delta^9$THCA-C-4A and/or B), $\Delta^9$-Tetrahydrocannabivarinsäure A ($\Delta^9$-THCVA-C3A), $\Delta^9$-Tetrahydrocannabiorcolsäure ($\Delta^9$-THCOA-C1 A and/or B), (−)-$\Delta^8$-trans-(6aR,10aR)-$\Delta^8$-tetrahydrocannabinol($\Delta^8$-THC-C5), (−)-$\Delta^8$-trans-(6aR,10aR)-Tetrahydrocannabinolsäure A ($\Delta^8$-THCA-C5A); (−)-(6aS,10aR)-$\Delta^9$-tetrahydrocannabinol ((−)-cis-$\Delta^9$-THC-C5); Cannabinol CBN-C5, cannabinol C4 (CBN-C4), Cannabivarin (CBN-C3), cannabinol C2 (CBN-C2), Cannabiorcol (CBN-C1), Cannabinolsäure A (C5 CBNA-A), Cannabinolmethylether (CBNM C-5) Cannabitriol-type (CBT): (−)-(9R,10R)-trans-Cannabitriol ((−)-trans-CBT-C5), (+)-(9S,10S)-Cannabitriol ((+)-trans-CBT C-5), (±)-(9R,10S/9S,10R)-Cannabitriol ((±)-cis-CBT-C5), (−)-(9R,10R)-trans [10-0-ethyl-cannabitriol] ((−)-trans-CBT-OEt-C5), (±)-(9R,10R/9S,10S)-Cannabitriol-C3 ((±)-trans-CBT-C3), 8,9-dihydroxy-Δ6a (10a) tetrahydrocannabinol (8,9-di-OH-CBT-C5), cannabidiolic A (CBDA C-59-OH-CBT-C5 ester), (−)-(6aR,9S,10S,10aR)-9,10-dihydroxy-hexahydrocannabinol, Cannabiripsol Cannabiripsol-C5, (−)-6a,7,10a-trihydroxy-$\Delta^9$-tetrahydrocannabinol ((−)-Cannabitetrol), 10-oxo-Δ6a (10a) tetrahydrocannabinol (OTHC); Cannabielsoin-like (CBE): (5aS, 6S, 9R, 9aR)-C5-Cannabielsoin (CBEC-5), (5aS, 6S, 9R, 9aR)-C3-Cannabielsoin (CBE C-3), (5aS, 6S, 9R, 9aR)-Cannabielsoinsäure A (CBEA-C5A), (5aS,6S,9R,9aR)-Cannabielsoinsäure B (CBEA-C5B), (5aS, 6S, 9R, 9aR)-C3-Cannabielsoinsäure B (CBEA-C3B), Cannabiglendol-C3 (OH-iso-HHCV C-3), Dehydrocannabifuran (DCBF C-5), Cannabifuran (CBF-C5); Isocannabinoide: (−)-$\Delta^7$-trans-(1R,3R,6R)-Isotetrahydrocannabinol,(±)-$\Delta^7$-1,2-cis-(1R, 3R,6S/1S,3S,6R)-Isotetrahydro-cannabivarin, (−)-$\Delta^7$-trans-(1R,3R,6R)-Isotetrahydrocannabivarin; (±)-(1aS,3aR,8bR, 8Cr-cannabicyclol (CBL-C5), (±)-(1aS,3aR, 8bR,8Cr-Cannabicyclolsäure A (CBLA-C5A) (±)-(1aS,3aR,8bR,8Cr-Cannabicyclovarin (CBLV C-3); Cannabicitran-type (CBT): Cannabicitran (CBT-C5); Cannabichromanon (CBCN C-5), Cannabichromanon-C3 (CBCN C-3), and Cannabicoumaronon (CBCON C-5).

In addition to the above cannabinoids, the carboxylic acids which are biosynthetic precursors of each are contemplated as cannabinoids of the technology. Examples of cannabinoids that may be present in the compositions of the present technology include THC, CBD, CBG, CBN, CBC, THCV, CBGA, CGCA, CBCA, THCA and CBDA.

All isomers, stereoisomers, enantiomers, of cannabinoids are contemplated to be within the scope of the present technology.

In some embodiments, the cannabinoid is present in the compositions of the present technology in an amount ranging from between about 0.5 wt % and about 10 wt % of the total weight of the composition. In some instances, the cannabinoid is present in the compositions of the present technology in an amount ranging from between about 2 wt % and about 8 wt %, or between about 2 wt % and about 6 wt %, or between about 2.5 wt % and about 5 wt %, or is present in an amount of about 2.5 wt %, or is present in an amount of about 5 wt %, or is present in an amount of about 6 wt % of the total weight of the composition.

ii) Anti-Inflammatory Agents

In some embodiments, the anti-inflammatory agents that may be included in the compositions of the present technology include, but are not limited to, nonsteroidal anti-inflammatory drugs, cyclooxygenase (COX) enzyme Inhibitors, Inhibitors of prostaglandin synthesis, reuptake inhibitors of endocannabinoids, antileukotrines, arachidonate 5-lipoxygenase inhibitors, leukotriene receptor antagonists, cysteinyl leukotriene receptor antagonists, and immune selective anti-inflammatory derivatives (ImSAIDs).

Other examples of anti-inflammatory agents that may be included in the compositions of the present technology include: Aspirin, Celecoxib, Diclofenac, Diflunisal, Etodolac, Ibuprofen, Indomethacin, Ketoprofen, Ketorolac, Nabumetone, Naproxen, Oxaprozin, Piroxicam, Salsalate, Sulindac, Tolmetin, Paracetamol, Phenylalanine-Glutamine-Glycine (FEG), D-isomeric form of FEG (feG).

In some implementations, the anti-inflammatory agent is synthetic (i.e., created using man-made chemicals rather than natural ingredients).

In some implementations, the anti-inflammatory agent is an anti-inflammatory analgesic.

In some embodiments, the anti-inflammatory agent is present in the compositions of the present technology in an amount of between about 0.5 wt % to about 90 wt %, or between about 1 wt % and about 90 wt % of the total weight of the composition, or is present in an amount of about 5 wt %, about 10 wt %, about 15 wt %, about 20 wt % or about 25 wt % of the total weight of the composition.

In some instances, the anti-inflammatory agent is present in an amount of between about 1 wt % and about 90 wt %, or between about 1 wt % and about 10 wt % or between about 5 wt % and about 10 wt %, or between about 20 wt % and about 90 wt %, or between about 30 wt % and about 90 wt %, or between about 40 wt % and about 90 wt %, or between about 50 wt % and about 90 wt %, or between about 60 wt % and about 90 wt %, or between about 70 wt % and about 90 wt %, or between about 80 wt % and about 90 wt %, or is present in an amount of about 85 wt %.

Other examples of components that may be present in the compositions of the present technology and that mat assist in relieving pain include phenolics and Polyphenolics. Examples of phenolics and polyphenolics include: Harpagoside, Boswellic acid, Gallic acid, Punicalagin, Oenothein B, Ellagic acid, Ellagitannins, Gallotannin, EGCG, Ferulic Acid, Salicylic acid, Methyl Salicylate, and Triethanolamine salicylate.

iii) Botanical Extract

In some embodiments, the botanical extracts useful in the compositions of the present technology include substances which are capable of imparting some anti-inflammatory effects when such substances are used in the compositions as defined herein and are administered to a subject. In some implementations of these embodiments, the botanical extracts of the present technology are also known for imparting analgesic effects when administered to a subject. As such, in those implementations, the botanical extracts of the present technology are also analgesic botanical extracts.

In some embodiments, the botanical extracts that may be included in the compositions of the present technology include, but are not limited to: *Boswellia* spp botanical and/or extract, *Curcuma* spp botanical and/or extract, *Camellia* spp botanical and/or extract, Green Tea botanical and/or extract, *Epilobium* spp botanical and/or extract, *Cannabis* spp botanical and/or extract, Cannflavin A, Glycosides of Cannflavin A, Luteolin, and Glycosides of Luteolin. Other examples of such compounds include: Capsaicinoids Extract, Caryophyllene Extract, Prenylated Flavones Extracts, Cannflavin A, Harpagoside Extract, Boswellic acid.

Other examples of botanical extracts that be used in the composition as defined herein include, but are not limited to: angelica extract, avocado extract, tasmannia lanceolata extract, wild yam extract, *Boswellia* spp. extract, fenugreek extract, *Harpagophytum* Spp. extract, hydrangea extract, althea extract, *Arnica* spp. extract, aloe extract, apricot extract, apricot core extract, *ginkgo* extract, fennel extract, turmeric extract, oolong tea extract, rose fruit extract, *echinacea* leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, sabdariffa extract, pyracantha fortuneana fruit extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, *salvia* extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocos extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, coix seed extract, mugwort extract, lavender extract, apple extract, lettuce extract, lemon extract, Chinese milk vetch extract, rose extract, rosemary extract, Roman and/or German chamomile extract and royal jelly extract.

In some embodiments, the botanical extract is present in the compositions of the present technology in an amount of between about 0.5 wt % to about 90 wt %, or between about 1 wt % and about 90 wt %, or between about 0.5 wt % to about 10 wt % of the total weight of the composition.

In some instances, the botanical extract is present in an amount of between about 1 wt % and about 25 wt %, or between about 10 wt % and about 90 wt %, or between about 20 wt % and about 90 wt %, or between about 30 wt % and about 90 wt %, or between about 40 wt % and about 90 wt %, or between about 50 wt % and about 90 wt %, or between about 60 wt % and about 90 wt %, or between about 70 wt % and about 90 wt %, or between about 80 wt % and about 90 wt %, or is present in an amount of about 85 wt %.

iv) Additional Components

In some embodiments, the compositions of the present technology comprise non-additional components which may, in some instances, assist in relieving pain in a subject.

Examples of additional components that may be present in the compositions of the present technology include are terpenes and terpenoids. Terpenes and terpinoids are the primary constituents of the essential oils of many types of plants and flowers. The terpenoids, sometimes called isoprenoids, are a large and diverse class of naturally occurring organic chemicals like terpenes, derived from five-carbon isoprene units assembled and modified in thousands of ways. Most are multicyclic structures that differ from one another not only in functional groups but also in their basic carbon skeletons. Well-known terpenoids include citral, menthol, camphor, salvinorin A in the plant *Salvia divinorum*, the cannabinoids found in *cannabis*, ginkgolide and bilobalide found in *Ginkgo biloba*, and the curcuminoids found in turmeric and mustard seed. The steroids and sterols in animals are biologically produced from terpenoid precursors. Sometimes terpenoids are added to proteins, e.g., to enhance their attachment to the cell membrane; this is known as isoprenylation.

Terpenes can be converted to terpenoids, synthetic terpenoids or semisynthetic terpenoids by an array of known chemical reactions. These conversions have been taught so exhaustively in the art that one of ordinary skill in synthetic organic chemistry or natural products chemistry would have no difficulty choosing the appropriate steps, sequences of steps and purification means necessary to prepare the subject terpenoid, synthetic or semisynthetic terpenoid and no more will be set forth here.

One group of terpenoids, together with one aroma associated therewith, includes; A/B-Pinene, Pine; Linalool, Lavender; B-Caryophyllene, Black pepper; Myrcene, Musk; Limonene, Citrus; Terpineol, Lilac; Nerolidol, Wood bark; Eucalyptol, Mint; Borneol, Camphor; A-Bisabolol, Floral; D-3 Carene, Pine; and Camphene, Herbal.

Another group of terpenoids includes: Beta-caryophyllene, Borneol, 1,8-cineole, camphene, Humulene, Limonene, Linalool, Myrcene, Nerolidol, Pulegone, and Terpinolene. Another preferred group of terpenoids includes: α-Pinene, β-Pinene, Myrcene, α-Phellandrene, LÏ3-Carene, α-Terpinene, β-Phellandrene, Limonene, cis-Ocimene, Terpinolene, β-Caryophyllene, α-Guaiene, Humulene, 6-Guaiene, Elemene, Guaiol, γ-Eudesmol, β-Eudesmol, Agarospirol, Bulnesol, and α-Bisabolol.

Another group of terpenoids includes: A-Pinene, Linalool, beta-Caryophyllene, Myrcene, and Limonene.

Flavonoids are other components that may be present in the compositions of the present technology. Flavonoids are a class of plant and fungus secondary metabolites. Chemically, flavonoids have the general structure of a 15-carbon skeleton, which consists of two phenyl rings (A and B) and heterocyclic ring (C). This carbon structure can be abbreviated C6-C3-C6. According to the IUPAC nomenclature, they can be classified into: flavonoids or bioflavonoids, isoflavonoids, derived from 3-phenylchromen-4-one (3-phenyl-1,4-benzopyrone) structure, and neoflavonoids, derived from 4-phenylcoumarine (4-phenyl-1,2-benzopyrone) structure. The three flavonoid classes above are all ketone-containing compounds, and as such, are anthoxanthins (flavones and flavonols). Flavonoids are widely distributed in plants, fulfilling many functions. Flavonoids are the most important plant pigments for flower coloration, producing yellow or red/blue pigmentation in petals designed to attract pollinator animals. In higher plants, flavonoids are involved in UV filtration, symbiotic nitrogen fixation and floral pigmentation. They may also act as chemical messengers, physiological regulators, and cell cycle inhibitors. Flavonoids secreted by the root of their host plant help *Rhizobia* in the infection stage of their symbiotic relationship with legumes like peas, beans, clover, and soy. *Rhizobia* living in soil can sense the flavonoids and triggers the secretion of Nod factors, which in turn are recognized by the host plant and can lead to root hair deformation and several cellular responses such as ion fluxes and the formation of a root nodule. In addition, some flavonoids have inhibitory activity against organisms that cause plant diseases, e.g. *Fusarium oxysporum*. Isoflavones use the 3-phenylchromen-4-one skeleton (with no hydroxyl group substitution on carbon at position 2). Examples include: Genistein, Daidzein, Glycitein, Isoflavanes, Isoflavandiols, Isoflavenes, Coumestans, and Pterocarpans.

One embodiment of flavonoids within the context of the technology includes: 6-OH-Luteolin 4'-methyl ether-7-(2"-a-rhamnoside-6'"-acetyl-b-glucoside); 6-OH-Luteolin 7-(6"-(E)-caffeoyl)-b-glucoside; Isoscutellarein 7-(2"-(6'"-acetyl)-b-allosyl)-b-glucoside; Isoscutellarein 4'-methyl ether-7-(2"-(6'"-acetyl)-b-allosyl)-b-glucoside; Apigenin 4'-(2"-(2'"-feruloyl-glucuronyl)-glucuronide); Apigenin 7-glucuronide-4'-(2"-(2'"-feruloyl-glucuronyl)-glucuronide); Apigenin 7-glucuronyl-4'-(2"-(2'"-E-p-coumaroyl-glucuronyl)-glucuronide); Luteolin 3'-b-glucoside-4'-(2"-a-rhamnosyl-b-glucoside); Luteolin 3',4'-di-b-glucoside; 5,7,4'-tri-OH-3'-OMe-Flavone 8-C-(2"-O-b-glucosyl-b-xyloside); 5,7-di-OH-3'-OMe-4'-Acetoxyflavone 8-C-(2"-O-b-glucosyl-b-xyloside); Iso-orientin 3'-methyl ether; 8-C-p-OH-Benzoyl-isovitexin 4'-glucoside; Apigenin 8-C-(2"-(4'"-acetyl-rhamnosyl)-glucoside); Spinosin; 6'"-Feruloyl-spinosin; Isoscoparin 7-glucoside; Carlinoside; Kaempferol 3-(6"-α-arabinosyl-glucoside); Kaempferol 3-(6"-α-arabinosyl-glucoside)-7-glucoside; Kaempferol 3-(2"-rhamnosyl-6"-malonyl-glucoside); Kaempferol 3-glucoside-7-(2"-(6'"-p-coumaroyl-glucosyl)-glucoside); 8-OMe-Kaempferol 3-(6"-malonyl-glucoside); Quercetin; Quercetin 4'-glucoside; Quercetin 3'-xyloside; Myricetin 3-(2"-acetyl-rhamnoside); Quercetin 3,4'-diglucoside; Isorhamnetin 3-rutinoside; Quercetin 3,7,4'-triglucoside; Isorhamnetin 3,7-diglucoside; Myricetin 3-(2"-rhamnosyl-glucoside); Myricetin 3'-(6"-p-coumaroyl-glucoside); Myricetin 7-(6"-galloyl-glucoside); Laricitrin 3-a-arabinofuranoside; Laricitrin 3-glucoside; Syringetin 3-(5"-glucosyl-a-arabinofuranoside); Syringetin 3-(6"-acetyl-glucoside); Syringetin 3-robinobioside; Syringetin 6-C-glucoside; 6,3'-di-OH-4,4'-di-OMe-5-Me-Aurone; 4,6,3',4'-tetra-OMe-Aurone (Z-form); 4,6,3',4'-tetra-OMe-Aurone (E-form); 6,3',4'-tri-OH-4-OMe-5-Me-Aurone; Maesopsin; Maesopsin 6-O-glucoside (two diastereoisomers); Licoagroaurone; 3'-formyl-4',6'-di-OH-2'-OMe-5-Me-Chalcone; Chalcononaringenin 2',4'-diglucoside; 2',4'-diOH-4'-OMe-6'-glucoside Dihydrochalcone; 2'-OH-3',4',6'-tri-OMe-Dihydrochalcone; Pelargonidin 3-glucoside-5-(6'"-acetyl-glucoside); Pelargonidin 3-(6"-feruloyl-glucoside)-5-(6'"-malonyl-glucoside); Cyanidin 3-(6"-malonyl-glucoside); Cyanidin 3-rutinoside; Cyanidin 3-(2",3"-digalloyl-glucoside); Cyanidin 3,4'-diglucoside; Delphinidin 3-(6"-acetyl-galactoside); Delphinidin 3'-(2"-galloyl-6"-acetyl-galactoside); Peonidin 3-rutinoside; Petunidin 3,7-diglucoside; Petunidin 3-(6"-E-p-coumaroyl-glucoside)-5-(6'"-malonyl-glucoside); Malvidin 3-(6"-E-p-coumaroyl-glucoside)-5-glucoside; Malvidin 3-(6"-Z-p-coumaroyl-glucoside)-5-glucoside; Malvidin 3-rutinoside-5-glucoside; Malvidin 3-(6"-(4'"-malonyl-rhamnosyl)-glucoside)-5-(6'"-malonyl-glucoside); Apigeninidin 5-glucoside; Luteolinidin 5-glucoside; Carboxypyrano Pelargonidin 3-glucoside; Carboxypyrano Cyanidin 3-glucoside; Carboxypyrano Cyanidin 3-(6"-malonyl-glucoside;); Carboxypyrano Malvidin 3-glucoside; Judaicin 7-(6"-acetyl-glucoside); Tectorigenin 4'-(6"-glucosyl-glucoside); 7-OH-6'-OMe-3',4'-methylenedioxyisoflavone 7-glucoside; Irisjaponin A; Irisjaponin B; Junipegenin B; Matteucinol 7-(6"-apiofuranosyl-b-glucoside); Hesperitin 7-(2"- galactosyl-6"-rhamnosyl-glucoside); Persicogenin 5,3'-di-OH-7,4'-di-OMe-flavanone; Naringenin 7-glucoside; Naringenin 7-(6"-galloyl-glucoside); Taxifolin 4'-glucoside; Aromadendrin 7-glucoside; Ampelopsin 7-glucoside; 2"-Accallunin; 2R,3R-trans-aromadendrin 7-(6"-(4'"-OH-2'"-methylenebutanoyl)-glucoside); (2R,3S)-(þ)-3',5-di-OH-4',7-di-OMe-Dihydroflavonol; 3-Desoxycallunin; Catechin 3-(6"-cinnamoyl-glucoside); Catechin 3-(2"-cinnamoyl-glucoside); Catechin 3-(2",6"-dicinnamoyl-glucoside); Anadanthoside; Cajanin; Indicanine C; 97. 6-(1,1-di-Me-allyl)-7,4'-di-OH-Flavan; 3-(4'-hydroxyphenyl)-5-methoxy-6-(3,3-dimethylallyl)-2",2"-dimethylchromene-(5",6": 8,7)-3-(propyl-2-one)-4H-1-benzo-2,3-Dihydropyran-2,4-dione; Maackianin 3-(6"-malonyl-glucoside); 3,4:8,9-Dimethylenedioxy-pterocarpan; Usararotenoid C; 12a-Epimillettosin; (þ)-Usararotenoid-B; [Catechin 3-glucoside-(4a->8)-catechin 3-(2"-cinnamoyl-glucoside)]; [Catechin 3-glucoside-(4a->8)-epicatechin 3-(6"-cinnamoyl-glucoside)]; Amentoflavone; Aulacomnium-biaureusidin; Cupressuflavone 7,7"-dimethyl ether; 4,4',6-tri-O-methyl-2-deoxymaesopsin-(2->7)-2,4,4',6-tetra-O-Methylmaesopsin; Catechin-(4a->8)-pelargonidin 3-glucoside; 2',2",2'"-tri-OH-4',4'"-di-OMe-4-O-5'"-bichalcone (Rhuschalcone 1); Puerarin (Daidzein 8-C-glucoside); Calycosin; Isoneorautenol; and Erybraedin A.

Another group of flavonoids includes: Apigenin, beta-Sitosterol, Orientin, Quercitrin, Apigenin-7-O-glucoside, Luteolin, Apigenin, Kaempferol, Cannflavin A, Cannflavin B, Myricetin, and Luteolin-7-O-glucoside.

Another group of flavonoids includes: Quercitrin, Apigenin-7-O-glucoside, Luteolin, Apigenin, Kaempferol, Cannflavin A, Cannflavin B, Myricetin, and Luteolin-7-O-glucoside.

In one embodiment, the cannabinoids useful in the compositions and methods of the present technology are naturally occurring, synthetic, biosynthetic, or semisynthetic cannabinoids.

In one embodiment, the terpenoids useful in the compositions and methods of the present technology are naturally occurring, synthetic, biosynthetic, or semisynthetic terpenoids.

In one embodiment, the flavonoids useful in the compositions and methods of the present technology are naturally occurring, synthetic, biosynthetic or semisynthetic flavonoids.

iv) Dosage Forms

Suitable dosages of the compositions for use in the methods of the present disclosure depend upon many factors including, for example, age and weight of an individual, at least one precise event requiring professional consultation, severity of an event, specific composition to be used, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

In some embodiments, the compositions of the present disclosure can be administered to a subject in need thereof as a therapeutic composition. As used herein, a "subject in need" refers to an individual at risk for or having a medical need such as those described herein. Additionally, a "subject in need" is also used herein to refer to an individual at risk for or diagnosed by a medical professional as having a condition described herein. As such, in some embodiments, the methods disclosed herein are directed to a subset of the general population such that, in these embodiments, not all the general population may benefit from the methods. Based on the foregoing, because some of the method embodiments of the present disclosure are directed to specific subsets or subclasses of identified individuals (that is, the subset or subclass of subjects "in need" of assistance in addressing one or more specific conditions noted herein), not all individuals will fall within the subset or subclass of subjects as described herein. Generally, the subject in need is a human. The subject in need can also be, for example, an animal such as a companion animal or a research animal such as, for example, a non-human primate, a mouse, a rat, a rabbit, a cow, a pig, and other types of research animals known to those skilled in the art. One primary reference describing dosage forms is Remington: The Science and Practice of Pharmacy, 21st ed., ISBN-13 9780781746731 ("Remington").

Suitable amounts of the active agent(s) for use in the dosage forms of the present disclosure will depend upon many factors including, for example, age and weight of an individual, specific active agent(s) to be used, nature of a composition, whether the composition is intended for direct administration or is a concentrate, and combinations thereof. Ultimately, a suitable amount can be readily determined by one skilled in the art. For example, one skilled in the art can begin with a low amount that can be increased until reaching the desired result or effect. Alternatively, one skilled in the art can begin with a high dosage that can be decreased until reaching a minimum dosage needed to achieve the desired result or effect.

For the purposes of the present technology, delivery includes the provision and use of a dosage form containing a composition of the technology so that about 10%, 20%, 30%, 40%, 50%, 60%, 70%, or 80%, more preferably, about 90%, and more preferably yet, about 95% of the composition of the technology reaches a biological system or material of the subject human or non-human such that it is available for biological interaction with said subject.

Dosage forms of the technology comprise non-medicinal ingredients or substances selected independently or in combination from cannabinoids, anti-inflammatory, and botanical extracts. Such substances may be lipophilic in nature with low solubility in hydrophilic biocompatible matrix materials. One method for obtaining desirable dosage forms comprising lipophilic substances and hydrophilic biocompatible matrix substances is to encapsulate or disperse lipophilic substances in the hydrophilic matrix using additives or modifiers which provide an environment for stable oil-in-water emulsions, micelles, liposomes or other complex phase equilibrium modified compositions.

A method of preparing a stable oil-in-water dosage form is to use a nanoemulsion to encapsulate lipophilic bioactive compounds in a carrier oil. The carrier oil is, optionally, food grade, not adversely affect product quality (such as appearance, taste, texture, or stability), protect from chemical degradation during storage and distribution, and increase bioavailability following ingestion. Carrier oils help stabilize emulsions from Ostwald ripening, a destabilization mechanism of nanoemulsions. This problem arises due to the increased solubility of dispersed phase in a hydrophilic. Carrier oils can have an effect the physicochemical stability of nanoemulsions in the gastrointestinal tract (GI Tract). The rate and extent of lipid digestion is higher for MCT emulsions than for LCT emulsions, which is attributed to differences in the water dispersibility of the medium and long chain fatty acids formed during lipolysis. The total bioavailability of active components after digestion can be higher for LCT emulsions than for MCT emulsions.

Long-chain triglycerides (LCT) contain fatty acids of 12-20 carbon atoms and can form mixed micelles with a hydrophobic core large enough to accommodate active substances such as THC and other cannabinoids, terpenoids and flavonoids. Medium-chain triglycerides (MCT) contain fatty acids of 12-20 carbon atoms and can form mixed micelles with smaller hydrophobic.

Emulsions can be prepared in concentrated form and later diluted several hundred times in sugar/acid solutions prior to consumption to produce finished dosage forms in either carbonated or non-carbonated biocompatible matrix systems. Selection of an emulsifier can affect the shelf-life and physicochemical properties of the emulsion. Emulsions stabilized by surfactants or other types of stabilizing compounds phospholipids, amphiphilic proteins, or polysaccharides, have been developed to provide controlled release, improved entrapment efficiency, and protection from degradation.

Other suitable types of non-medicinal ingredients include natural emulsifiers, oils, thickening agents, minerals, acids, bases, vitamins, flavors, colorants and other processing, storage, distribution, transport, and use conditions such as ultrasonication, nitrogen dosing, packaging, and sterilization.

Emulsions can be prepared several ways such as mechanical processes which employs shear force to break large emulsion droplets into smaller ones, high-pressure homogenization (HPH, including microfluidization) and high-amplitude ultrasonic processing, and ultrasound-assisted emulsification. Small droplet sizes lead to transparent emulsions. Droplet sizes about 100, 90, 80, 70, 60, 50 or 40 nm are desirable. Preferably the droplet sizes for transparent emulsions are in the range of 40 to 60 nm, more preferably they are 45 to 55 nm, more preferably yet, 50 nm.

Nutritional additives and modifiers comprise substances useful to the consumer of the oral dosage form for maintenance of normal body health. Preferably nutritional additives comprise essential nutrients including vitamins, dietary minerals amino acids and fatty acids vitamin A, vitamin B1, vitamin B2, vitamin B3, vitamin B5, vitamin B6, vitamin B7, vitamin B9, vitamin B12, vitamin C, vitamin D, vitamin E, vitamin K calcium, phosphorus, potassium, sulfur, sodium, chlorine, magnesium, iron, cobalt, copper, zinc, molybdenum, iodine, selenium, manganese, nickel, chromium, fluorine, boron, strontium histidine, isoleucine, leucine, lysine, methionine, cysteine, phenylalanine, tyrosine, threonine, tryptophan, valine, alpha-linoleic acid, and linoleic acid.

Optional additives and modifiers comprise one or more of acids, bases, acidity regulators, alcohol, anticaking agents, antifoaming agents, antioxidants, bulking agents, coagulation agents, food coloring, color retention agents, emulsifiers, flavor enhancers, flour treatment agents, gelling agents, glazing agents, humectants, leavening agents, tracer gases, preservatives, stabilizers, sweeteners, tenderizers, and thickeners. One class of common additive or modifier useful in oral dosage forms of the technology is the group of substances referred to as phospholipids. Phospholipids are made up of two fatty acid tails and a phosphate group head. Fatty acids are long chains mostly made up of hydrogen and carbon, while phosphate groups consist of a phosphorus molecule with four oxygen molecules attached. These two components of the phospholipid are connected via a third molecule, glycerol. Phospholipids can act as emulsifiers, enabling oils to form a colloid with water. Phospholipids are one of the components of lecithin which is found in egg-yolks, as well as being extracted from soy beans, and is used as a food additive in many products and can be purchased as a dietary supplement. Lysolecithins are typically used for water-oil emulsions like margarine, due to their higher HLB ratio.

Dosage forms of this type commonly use phospholipid additives or modifiers to solubilize one or more hydrophobic components of the *cannabis* or *cannabis* derived composition. In this embodiment, phospholipids are typically derived from natural sources such as a naturally occurring oils from a plant such as coconut, safflower and sunflower. These phospholipids can include secondary products obtained therefrom such as lecithin from sunflower oil. In these embodiments the phospholipid or derivative therefrom is present in about 0.01-10 weight or volume percent. More typically, 0.01, 0.1, 1 or 10 weight or volume percent, more typically yet 0.1 to 1 weight or volume percent.

In embodiments wherein triglycerides are used as additives or modifiers of the oral dosage form, they are present in about 0.01-10 weight or volume percent. More typically, 0.01, 0.1, 1 or 10 weight or volume percent, more typically yet 0.1 to 1 weight or volume percent.

Natural phospholipid derivatives include egg PC (Egg lecithin), egg PG, soy PC, hydrogenated soy PC, and sphingomyelin as natural phospholipids. Synthetic phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), phosphatidylserine (DOPS), PEG phospholipid (mPEG-phospholipid, polyglycerin-phospholipid, functionalized-phospholipid, and terminal activated-phospholipid).

Phospholipids can form cell, micelle and liposomal membranes as well as other self-organizing multi-molecular structures because the phosphate group head is hydrophilic (water-loving) while the fatty acid tails are hydrophobic (water-hating). They automatically arrange themselves in a certain pattern in water or other polar environment because of these properties, and form membranes. To form membranes, phospholipids line up next to each other with their heads on the outside of the polar medium and their tails on the inside, thus forming an inner and outer surface. A second layer of phospholipids also forms with heads facing the inside of the structure and tails facing away. In this way, a double layer is formed with phosphate group heads on the outside, and fatty acid tails on the inside. This double layer, called a lipid bilayer, forms the main part of the membrane or other similar structure.

Extraction in natural products chemistry is a separation process comprising the separation of a substance from a matrix of natural materials and includes liquid-liquid extraction, solid phase extraction and what is commonly referred to as super-critical extraction. The distribution of any given compound or composition (hereinafter desired material) between two phases is an equilibrium condition described by partition theory. This is based on exactly how the desired material moves from a first solution, typically water or other material capable of dissolving a desired material with a first solubility of the desired material, into second material, typically an organic or other immiscible layer having a second solubility of the desired material layer.

One of ordinary skill in the art of natural products extraction and isolation could devise many more methods of fractionating said desired materials and no further need be described here. Once various fractions of desired material have been obtained by any method such as any of the above described fractionation and purification methods, any number of the fractions can be recombined. The recombination can be by simple mixing or by various mechanical.

In some embodiments, the compositions of the present technology is an oral dosage form, a sublingual dosage form, a transdermal dosage form, a topical dosage form, a topical gel dosage form, an oral spray dosage form, a nasal dosage form, an ophthalmic dosage form, a suppository dosage form, all of which are known by one of ordinary skill in the arts of pharmaceutical or pharmacological practice as described in Remington: The Science and Practice of Pharmacy, 21st ed., ISBN-13 978-0781746731, which is incorporated by reference herein in its entirety and with specificity.

In some embodiments, the oral dosage forms of the technology may comprise cannabinoid, terpenoid or flavonoid metabolites such as bio-metabolites, primary and secondary metabolites described herein. Oral dosage forms of the technology further comprise cannabinoid, terpenoid or flavonoid derivatives such as chemical derivatives, stereo- and regioisomers, conformationally locked, cyclization, ring-opened compounds, oxidized-, reduced-, or halo-substituted derivatives as described herein. Oral dosage forms of the technology may comprise cannabinoid, terpenoid or flavonoid prodrugs such as ethers, esters, lactones, carbonates or their nitrogen, sulfur or phosphorous analogs as described herein. Oral dosage forms of the technology comprise delivery systems impacting organoleptic properties of *cannabis* including physical structures such as membranes, micelles, lipids, droplets, or foams as described herein. Oral dosage forms of the technology may comprise delivery systems as described herein. Oral dosage forms of the technology may comprise *cannabis* or *cannabis* derived compositions and one or more non-*cannabis* or non-*cannabis* derived physiologically active substance such as a stimulant, depressant, intoxicant or other experience modifying ingredient described herein.

In such embodiments wherein the compositions of the present technology are in a beverage form, the cannabinoid may be formulated together with one or more lipid excipient to enhance the bioavailability. In some embodiments, the lipid excipient is an oil comprising long-chain triglycerides (LCT). In general, LCT contain fatty acids of 12-20 carbon atoms and can form mixed micelles with a hydrophobic core large enough to accommodate the cannabinoid. LCT may be a mixture of long-chain mono-, di- and triglycerides (which may be present in varying ratios), or may consist predominantly of triglycerides. LCT may be obtained from plant, animal or fungal sources. In some embodiments, the LCT is of vegetable origin, such as corn, canola, soybean and the like. In some embodiments, the lipid excipient is glyceryl monolinoleate, which is sold under the tradename Maisine®CC. Maisine®CC consists of mono-, di- and triglycerides of mainly linoleic ($C_{18:2}$) and oleic ($C_{18:1}$) acids, the diester fraction being predominant. Maisine®CC contains 32-52% of monoglycerides; 40-55% of diglycerides; and 5-20% of triglycerides. It is derived from corn oil by an alcoholysis reaction between glycerol and refined corn oil, followed by a winterization process to eliminate certain saturated mono-, di- and triglycerides. In such embodiments, the composition of the present technology thus comprises cannabinoid and Maisine®CC.

In one embodiment, the present technology is directed to any of the above embodiments wherein a composition of the technology is provided in a device for delivery of the composition to a consumer comprising; a container suitable for holding a maximum amount of the composition; a provisioning mechanism for providing a dose of the composition to the consumer; and a metering system transporting the composition to the provisioning mechanism; such that the amount of composition delivered to the consumer is controlled by the metering system.

As an example of the use of the compositions of the technology, dosage forms, delivery methods, devices and kits, the following description is directed to pain disorders of subjects. In the context of the present disclosure, subjects include: humans and animals. Animals include: rabbits, hedgehogs, alpacas, camels, cats, cows, dogs, donkeys, ferrets, goats, horses, llamas, pigs, foxes, rodents, sheep and birds such as parrots and passerines, namely finches and canaries. Preferably, companion animals include cats, dogs, ferrets, goats, horses, and birds such as parrots. More preferably, cats, dogs, and parrots. When considering pain in companion animals, several types are exemplary. Pain related to joint and muscle is typical, however neurological pain is also contemplated.

In one embodiment, the present technology comprises a composition described herein in a dosage form for transmucosal administration. Said dosage form further comprising one or more active lipophilic compounds which are components of the compositions of the technology, a polymeric matrix formed by two or more water-soluble polymers and a rapid dissolution agent. At least one of the water-soluble polymers is an amphiphilic polymer and at least one is either a hydrophilic polymer or an amphiphilic polymer with a hydrophobic-hydrophilic balance different from the first amphiphilic polymer. In addition, the polymeric matrix is not crosslinked, and no covalent interaction occurs between the two or more polymers and between the polymers and said lipophilic active compound or compounds, which is interwoven with the aforesaid polymeric matrix. Such dosage forms, methods and devices are disclosed in US 2017/0119660 A1, May 4, 2017, and WO 2017/072774 A1, May 4, 2017, the contents of which are herein incorporated in their entirety by reference thereto with specificity.

In one embodiment, the present technology comprises a composition described herein in a dosage form contained within devices and methods for preparing, managing, and/or administering metered doses of a composition described herein for vaporized administration. In some embodiments, dose cartridges comprising at least one composition described herein include a heating element integrated into the cartridge in close contact with said composition. In some embodiments, cartridge-mounted doses are stored in a magazine, optionally in carousel form, before use. Transport of a cartridge from a magazine to an electrically operated vaporizing chamber which activates the heating element is provided by a mechanical pickup means. Such devices and methods are disclosed in US 2017/0119979 A1, May 4, 2017, the content of which is incorporated by reference herein in its entirety and with specificity.

In one embodiment, the present technology comprises a composition described herein in an inhaler dosage form and device for pulmonary delivery of at least one composition described herein from a drug dose cartridge to an inhaling user, comprising: a first conduit for conducting a carrier airflow to a proximal opening of a mouthpiece for use by the user; a holder configured to position the dose cartridge within the carrier airflow; and a second conduit for conducting a shunting airflow to the mouthpiece without passing through the dose cartridge position. In some embodiments, a controller connected to a valve controls a rate of carrier airflow, for example by controlling the shunting airflow, based on a sensor indication of airflow rate and a target airflow profile. Such inhaler devices, without a composition of the technology, are disclosed in US 2017/0119981 A1, May 4, 2017, and WO 2017/0106153 A1 Apr. 20, 2017, the contents of which are incorporated by reference herein in their entirety and with specificity.

In one embodiment, the present technology comprises a composition described herein in a dosage form further comprising mucus penetrating particles (MPPs) include one or more core polymers, one or more compositions of the technology; and one or more surface modifying agents. The surface modifying agents coat the surface of the particle in a sufficient density to enhance the diffusion of the modified nanoparticles throughout the mucosa, relative to equivalent nanoparticles that are not surface modified. Nanoparticles can be sufficiently densely coated with poly (ethylene glycol) (PEG) with a molecular weight of from 10 kD to 40 kD or greater coated with a surface density from about 0.1 to about 100 molecules/100 $nm^2$, preferably from about 0.5 to about 50 molecules/100 $nm^2$, more preferably from about 0.9 to about 45 molecules/100 $nm^2$. Such mucus penetrating particles are disclosed in WO 2017/075565 A1, May 4, 2017, the contents of which is incorporated by reference herein in its entirety and with specificity. The present technology comprises a composition described herein in an ingestible dosage form further comprising drug delivery device configured for wireless communication with other ingestible drug delivery devices which further comprise a compound of the technology. Such devices are disclosed in US 2017/0106178 A1, Apr. 20, 2017, EP 3151906 A1, Apr. 12, 2017, US 2015/343144 A1, Dec. 3, 2015, U.S. Pat. No. 9,662,392 B2, May 30, 2017, WO 2015/187289 A1, Dec. 10, 2015 the contents of which are incorporated by reference herein in their entirety and with specificity.

In one embodiment, the present technology comprises a composition described herein in a dosage form further comprising an inhaler-delivery-device-packaged homogenate of solid heterogeneous-lipid particulates carrying a composition of the technology, wherein the solid heterogeneous-lipid particles comprise: one (or more) lipid(s) whose melting point(s) is (are) substantially above room temperature; in combination with, one (or more) lipid(s) whose melting point(s) is (are) substantially less than room temperature. Such inhaler-delivery-device-packages are disclosed in WO 2017/054071 A1 Apr. 6, 2017, the contents of which is incorporated by reference herein in its entirety and with specificity.

In one embodiment, the present technology comprises a composition described herein in a dosage form further comprising phospholipid nanoparticle compositions of a composition described herein formed from phospholipids and simpler lipids in an unfired sequential process that encapsulate a high concentration of cannabinoids, and create standardized precision-metered dosage forms of a composition of the technology; yielding an increase cannabinoid transport across hydrophobic mucosa; increase the bioavailability of the cannabinoid 1, 2, 3, 4, 5, 6, 7, 8, 9, 10, 11 to 12-fold, preferably 4-fold to 10-fold, more preferably 2-fold to 8-fold, decrease the dose of cannabinoids reduced amount of cannabinoids needed to illicit the same therapeutic effect compared to raw and non-encapsulated cannabinoids; where the nanoparticle dynamic structure reduces the adverse effects of cannabinoids; and enable safe more efficacious cannabinoid therapy. Such nanoparticles are disclosed in US 2017/0000744 A1, Jan. 5, 2017, the content of which is incorporated by reference herein in its entirety and with specificity.

In one embodiment, the present technology comprises a composition described herein in a dosage form further comprising a device and method comprising receiving, in a mixing chamber, a first amount of a first composition described herein from a first container, receiving, in the mixing chamber, a second amount of a second composition described herein from a second container, mixing the first amount of the first composition and the second amount of the second composition to create a mixed composition, vaporizing the mixed composition to create a vapor, and expelling the vapor through an exhaust port for inhalation by a user. Such methods and devices are disclosed in US 2016/03255055 A1, Nov. 10, 2016, the content of which is incorporated by reference herein in its entirety and with specificity.

In one embodiment, the present technology comprises a composition described herein in a sublingual dosage form further comprising a composition of the technology, and a dispenser for delivering at least one pharmacologically active cannabinoid from the composition described herein contained inside the dispenser into the sublingual cavity of a subject when the dispenser is placed within the subject's sublingual cavity with the composition described herein contained therein. Also disclosed are a method and apparatus for preparing the sublingual dosage form, and compositions and kits comprising the sublingual dosage form. Such dosage forms, methods and devices are disclosed in US 2016/0296464 A1, Oct. 13, 2016, the content of which is incorporated by reference herein in its entirety and with specificity.

In one embodiment, the compositions of the present technology comprise no more than 100 µg/g delta-9-tetrahydrocannabinol (THC), or no more than 10 µg/g delta-9-tetrahydrocannabinol (THC), or no more than 1 µg/g delta-9-tetrahydrocannabinol (THC). In one embodiment, the compositions of the present technology comprise less than 100, 90, 80, 70, 60, 50, 40, 30, 20, 10, 1, 0.1, 0.01, or 0.001 µg/g delta-9-tetrahydrocannabinol (THC).

In one embodiment, the compositions of the present technology comprise CBC, CBG, beta-caryophyllene (BCP), diindolymethane (DIM), an alkylamide found in or produced by *Echinacea*, a falcarinol found in or produced by carrots, celery, parsley or *Panax ginseng*, a yangonin, or a yangonin found in or produced by the Kava plant (*Piper methysticum*).

In one embodiment, the compositions of the present technology comprise beta-caryophyllene (BCP), diindolymethane (DIM), an alkylamide found in or produced by *Echinacea*, a falcarinol found in or produced by carrots, celery, parsley or *Panax ginseng*, a yangonin, or a yangonin found in or produced by the Kava plant (*Piper methysticum*).

EXAMPLES

The examples below are given so as to illustrate the practice of various embodiments of the present disclosure. They are not intended to limit or define the entire scope of this disclosure. It should be appreciated that the disclosure is not limited to the particular embodiments described and illustrated herein but includes all modifications and variations falling within the scope of the disclosure as defined in the appended embodiments.

Example 1—Topical Compositions for Relieving Pain

TABLE 1

Topical compositions

| Composition # | Ingredients |
|---|---|
| 1 | 5% w/w CBD |
|   | 1% w/w diclofenac |
|   | 94% w/w non-medicinal ingredients |
| 2 | 5% w/w CBD |
|   | 15% w/w triethanolamine salicylate |
|   | 80% w/w non-medicinal ingredients |
| 3 | 2.5% w/w CBD |
|   | 15% w/w methyl salicylate |
|   | 3% w/w menthol |
|   | 3% w/w camphor |
|   | 1% w/w *eucalyptus* |
|   | 75.5% w/w non-medicinal ingredients |
| 4 | 5% w/w CBD |
|   | 3% w/w menthol |
|   | 3% w/w methyl salicylate |
|   | 2% w/w capsaicin |
|   | 87% w/w non-medicinal ingredients |
| 5 | 5% w/w CBD |
|   | 15% w/w methyl salicylate |
|   | 25% w/w *arnica* extract |
|   | 55% w/w non-medicinal ingredients |
| 6 | 5% w/w CBD |
|   | 2.5% w/w ibuprofen |
|   | 92.5% w/w non-medicinal ingredients |

To prepare the compositions outlined in Table 1, water soluble ingredients are weighed into a suitable vessel and heated in a water bath while mixing with a propeller stirrer. The water insoluble ingredients are weighed into a suitable vessel and mixed well. The mixture is heated on a hot plate using a propeller stirrer at slow speed. A coarse emulsion is prepared by gradually adding the water insoluble phase into the water soluble phase. The coarse emulsion is homogenized. Homogenization is stopped and the mixture is then mixed with a propeller mixer to allow the mixture to congeal and form a homogenous product.

INCORPORATION BY REFERENCE

All references cited in this specification, and their references, are incorporated by reference herein in their entirety where appropriate for teachings of additional or alternative details, features, and/or technical background.

EQUIVALENTS

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following embodiments.

The invention claimed is:

1. A composition for topical application comprising:
at least one purified cannabinoid, wherein the purified cannabinoid is cannabidiol (CBD);
at least one anti-inflammatory agent in an amount ranging from between about 10 wt % and about 90 wt % of the total weight of the composition, wherein the anti-inflammatory agent is methyl salicylate; and
at least one botanical extract, wherein the botanical extract is *arnica*.

2. The composition of claim 1, further comprising a terpene or terpenoid.

3. The composition of claim 2, wherein the terpene or terpenoid is menthol, camphor, or a combination thereof.

4. The composition of claim 2, wherein the terpene is an isolate, an extract or a distillate.

5. The composition of claim 1, further comprising a flavonoid, wherein the flavonoid is an isolate, an extract or a distillate.

6. The composition of claim 1, wherein the purified cannabinoid is present in an amount ranging from between about 0.5 wt % and about 10 wt % of the total weight of the composition.

7. The composition of claim 1, wherein the purified cannabinoid is present in an amount ranging from between about 2 wt % and about 8 wt % of the total weight of the composition.

8. The composition of claim 1, wherein the purified cannabinoid is present in an amount ranging from between about 2 wt % and about 6 wt % of the total weight of the composition.

9. The composition of claim 1, wherein the anti-inflammatory agent is present in an amount ranging from between about 10 wt % and about 25 wt % of the total weight of the composition.

10. The composition of claim 1, wherein the anti-inflammatory agent is present in an amount ranging from between about 20 wt % and about 90 wt % of the total weight of the composition.

11. The composition of claim 1, wherein the anti-inflammatory agent is present in an amount of, about 10 wt %, about 15 wt %, about 20 wt % or about 25 wt % of the total weight of the composition.

12. The composition of claim 1, wherein the botanical extract is present in an amount ranging from between about 0.5 wt % and about 90 wt % of the total weight of the composition.

13. The composition of claim 1, wherein the botanical extract is present in an amount ranging from between about 1 wt % and about 25 wt % of the total weight of the composition.

14. The composition of claim 1, wherein the botanical extract is present in an amount ranging from between about 0.5 wt % and about 10 wt % of the total weight of the composition.

15. A composition for topical application comprising:
at least one purified cannabinoid in an amount of between about 0.5 wt % and about 10 wt % of the total weight of the composition, wherein the purified cannabinoid is cannabidiol (CBD);
at least one anti-inflammatory agent in an amount of and about 10 wt % of the total weight of the composition, wherein the anti-inflammatory agent is methyl salicylate; and
at least one botanical extract in an amount of between about 1 wt % and about 25 wt % of the total weight of the composition, wherein the botanical extract is *arnica*.

16. A composition for topical application comprising:
at least one purified cannabinoid, wherein the purified cannabinoid is cannabidiol (CBD);
at least one anti-inflammatory agent in an amount of between about 10 wt % and about 90 wt % of the total weight of the composition, wherein the anti-inflammatory agent is methyl salicylate;

at least one botanical extract in an amount of between about 0.5 wt % and about 90 wt % of the total weight of the composition, wherein the botanical extract is *arnica*, and a terpene or terpenoid, wherein the terpene or terpenoid is menthol, camphor, or a combination thereof.

17. A method for relieving pain in a subject, the method comprising administering to the subject the composition as defined in claim 1.

\* \* \* \* \*